United States Patent

Teixido

[11] Patent Number: 5,846,192
[45] Date of Patent: Dec. 8, 1998

[54] POLYMERIC SURGICAL RETRACTOR

[75] Inventor: Ruben A. Teixido, Wilmington, Del.

[73] Assignee: Teixido-Longworth Partnership, Greenville, Del.

[21] Appl. No.: 962,384

[22] Filed: Oct. 31, 1997

[51] Int. Cl.[6] .................................................. A61B 17/02
[52] U.S. Cl. ......................................... 600/210; 600/201
[58] Field of Search .................... 600/201, 210, 600/214, 217, 206, 208

[56] References Cited

U.S. PATENT DOCUMENTS

| | | | |
|---|---|---|---|
| 2,666,428 | 1/1954 | Glenner | 600/210 |
| 2,831,480 | 4/1958 | Milano | 600/210 |
| 3,651,800 | 3/1972 | Wilbanks | 600/210 |
| 3,863,627 | 2/1975 | Bouffard | 600/210 |
| 4,048,987 | 9/1977 | Hurson | 600/210 |
| 4,421,107 | 12/1983 | Estes et al. . | |
| 4,562,832 | 1/1986 | Wilder et al. | 600/210 |
| 4,686,972 | 8/1987 | Kurland | 600/210 |
| 5,213,114 | 5/1993 | Bailey, Jr. | 600/208 |
| 5,231,974 | 8/1993 | Giglio et al. | 600/206 |
| 5,370,109 | 12/1994 | Cuny . | |
| 5,454,365 | 10/1995 | Bonutti . | |
| 5,460,170 | 10/1995 | Hammerslag . | |

*Primary Examiner*—Paul J. Hirsch
*Attorney, Agent, or Firm*—Huntley & Associates

[57] ABSTRACT

A surgical retractor made of polymeric material is provided for use especially with electric scalpels.

8 Claims, 1 Drawing Sheet

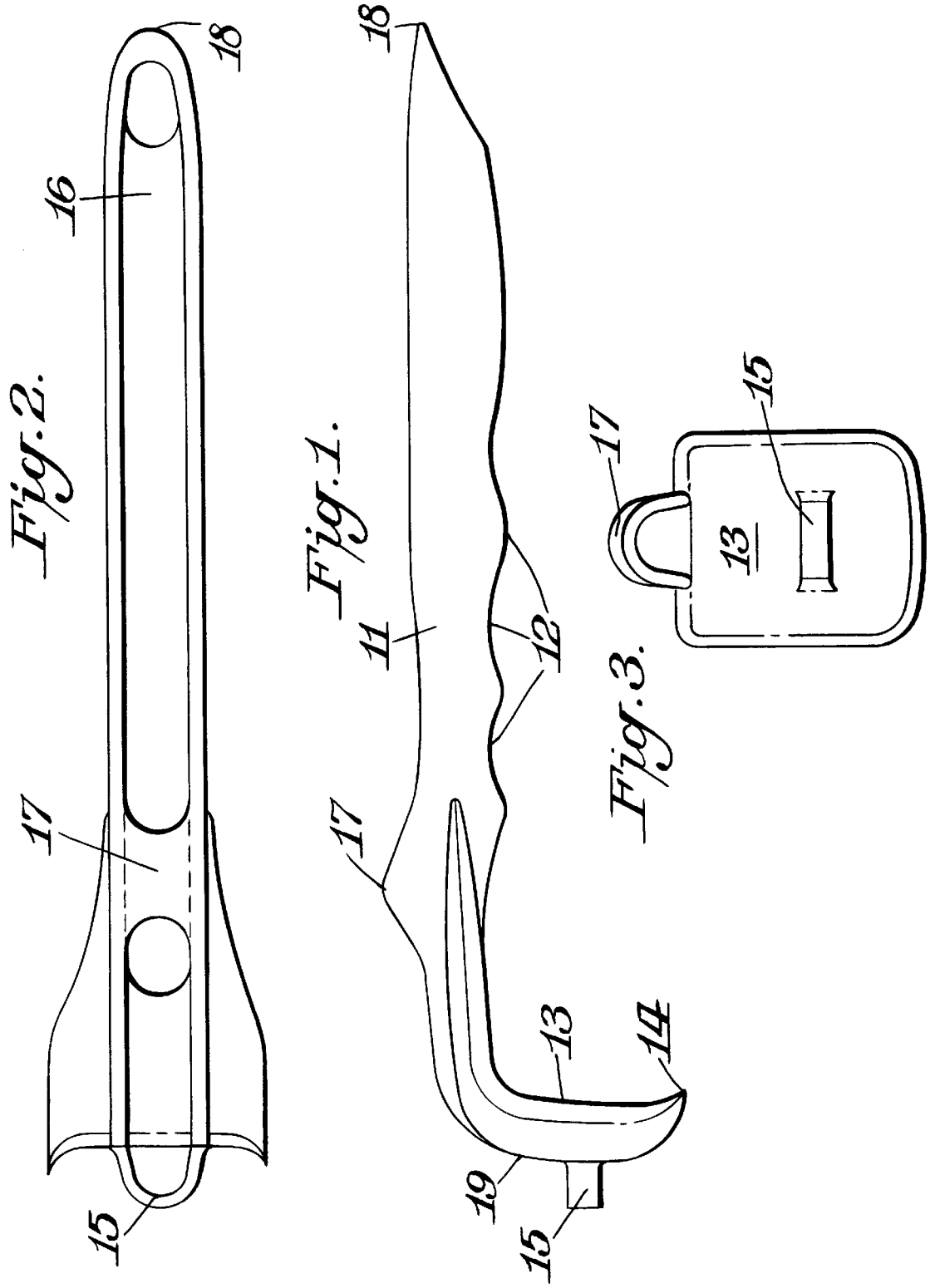

POLYMERIC SURGICAL RETRACTOR

BACKGROUND OF THE INVENTION

Surgical retractors are widely used in a variety of surgical procedures. Specifically, retractors are used during operations to assist medical personnel by restraining or moving tissue and organs away from the area upon which the surgery is to be performed.

With the advent of new surgical devices such as electric scalpels and laser scalpels, it has become necessary to modify the design and construction of surgical retractors. Specifically, the use of electric scalpels requires a surgical retractor designed to protect the tissue in contact with the retractor from exposure to the electrical energy discharged by the electric scalpel. Also, it is important to protect the surgeon and other operating personnel from this same electrical energy discharged by the electric scalpel. Traditionally, surgical retractors have been constructed from metals, such as stainless steel, because of the ease of manufacture and sterilization of such materials. Unfortunately, such materials do not provide protection from the electrical energy discharged by electric scalpels.

Electric scalpels operate by discharging a directed electrical energy stream. Surgeons are able to direct these electrical energy streams precisely to the areas upon which the surgery is to be performed. However, because of their proximity to the surgical site, the retractors are often also exposed to the electrical energy stream. This results in two difficulties if the retractor is not electrically insulated. First, an electrically conductive retractor may result in the electrical energy stream being misdirected toward tissue which is not to be operated upon. Secondly, electrically conducting retractors may also redirect the electrical energy stream toward the medical personnel, causing not only discomfort but also increasing the potential for interference with the dexterity of the medical personnel.

Therefore, surgical retractors constructed of an electrically insulating material are desirable. In addition, the material of construction must be sterilizable and autoclavable to allow for the necessary sterilization process so the retractors may be reused for multiple, successive surgical procedures.

SUMMARY OF THE INVENTION

In order to meet the requirements for use with electric scalpels, the present invention provides a surgical retractor which is made from an electrically insulating material.

Specifically, the present invention provides a surgical retractor of polymeric material comprising a proximal handle having a top and a bottom, a gripping means on the bottom of the handle, a substantially open channel on the top of the handle that is of a size and configuration to accommodate a suction tube, a distal blade positioned at a substantially right angle to the handle, and a rearwardly extending undercut at the end of the blade.

BRIEF DESCRIPTION OF THE DRAWINGS

FIG. 1 is a side view of a surgical retractor of the present invention.

FIG. 2 is a top view of a surgical retractor of the present invention.

FIG. 3 is a front view of the distal end of a surgical retractor of the present invention.

DETAILED DESCRIPTION OF THE INVENTION

The present retractors are prepared from polymeric materials. Polymeric materials are particularly well suited for this application because of their capability of being readily molded and formed into complex shapes. The polymeric materials can be thermoplastic or thermoset. Two polymeric materials which are particularly useful are polyetherimide and polyimide. Liquid crystal polymers (LCPs) can also be used. Preferred thermosetting materials which can be used include phenolic and melamine resins.

Referring now to the figures, the features of the present surgical retractors will be described in detail. As seen in FIG. 1, which is a side view of the retractor, the retractor has a proximal handle 11. Handle 11 has a gripping means 12 on the bottom of the handle. The gripping means 12 shown in FIG. 1 is a series of undulations designed to conform to the hand of the user. Other gripping means may be utilized, as will be evident to the skilled designer.

The retractor is also provided with a distal blade 13 at the distal end of handle 11. Blade 13 is positioned at a substantially right angle to handle 11. Blade 13 is preferably provided with rearwardly extending undercut 14 at the end of the blade. In a preferred embodiment, retractor is provided with retaining ring 15 which can be used to retain a suction tube (not shown) or devices of similar configurations such as fiber optic lighting devices.

In FIG. 2, the retractor is viewed from the top side. Open channel 16 is configured to allow a suction tube (not shown) or other similar devices to be contained within the retractor. This allows for suction (or other required services such as light) to be made available to the medical personnel at the distal end of the retractor. Constraint 17 is preferably provided to help guide a suction tube or other similarly configured device as it passes through the open channel 16 and into the retaining ring 15 on the distal end of the retractor.

FIG. 3 shows a view of the distal end of the retractor. The distal blade 13, retaining ring 15 and constraint 17 are seen in this Figure.

The overall length of the retractor will necessarily vary with the intended use, but is generally about from 6 to 12 inches. For specialized applications such as breast surgery, a length of about from 7 to 9 inches is preferred, with an overall length of about from 7.5 to 8 inches being particularly preferred for this application. In a most preferred embodiment, the overall length of the retractor is about 7.75 inches. The overall length of the retractor is measured from the proximal end 18 to the face 19 of the distal blade 13 (See FIG. 1) and does not include the retaining ring 15 in that measurement.

Although as previously discussed, any number of polymeric materials may be used for the retractor of the present invention, thermoplastic materials have been found to be especially well suited for this application. Polyetherimides are preferred, for their excellent high heat deflection temperature, and good processability, facilitating rapid production of injection molded parts. Such materials are well known in the art, as described, for example, in Floryan et al., "Polyetherimide: more information on a new high-performance resin", Modern Plastics 1982, pp 146–151. A preferred material which has been found to be especially well suited is ULTEM® polyetherimide resin available from the General Electric Company. This resin has been shown to have suitable retention of mechanical properties, such as potential yield strength, impact strength and lipid resistance, even after being subjected to numerous sterilizations by steam autoclave or chemical vapor sterilization processes. This allows a retractor made from such a material to be used for multiple surgical procedures before requiring replacement.

I claim:

1. A reusable and sterilizable surgical retractor consisting essentially of polymeric material selected from at least one of the group consisting of polyetherimide, polyimide and thermosetting material comprising a proximal handle having a top and a bottom, a gripping means on the bottom of the handle, a substantially open channel on the top of the handle of a size and a configuration to accommodate a suction tube, a distal blade positioned at a substantially right angle to the handle, and a rearwardly extending undercut at the end of the blade.

2. A surgical retractor of claim 1, wherein the polymeric material consists essentially of polyetherimide.

3. A surgical retractor of claim 1, wherein the polymeric material consists essentially of polyimide.

4. A surgical retractor of claim 1, wherein the length of the retractor is about from 6 to 12 inches.

5. A surgical retractor of claim 4, wherein the length of the retractor is about from 7 to 9 inches.

6. A surgical retractor of claim 1, wherein the polymeric material consists essentially of a thermosetting material.

7. A surgical retractor of claim 6, wherein the thermosetting material consists essentially of phenolic.

8. A surgical retractor of claim 6, wherein the thermosetting material consists essentially of melamine.

\* \* \* \* \*